United States Patent [19]

Kleiner

[11] Patent Number: 5,705,670

[45] Date of Patent: Jan. 6, 1998

[54] PROCESS FOR THE PREPARATION OF ALKALI METAL SALTS OF PHOSPHONIC ACID MONOMETHYL ESTERS

[75] Inventor: Hans-Jerg Kleiner, Kronberg, Germany

[73] Assignee: Hoechst Aktiengesellschaft, Germany

[21] Appl. No.: 599,485

[22] Filed: Jan. 24, 1996

[30] Foreign Application Priority Data

Jan. 26, 1995 [DE] Germany ............... 195-02 331.5

[51] Int. Cl.$^6$ ........................................ C07F 9/40
[52] U.S. Cl. ............................................... 558/131
[58] Field of Search ................................... 558/131

[56] References Cited

U.S. PATENT DOCUMENTS

| | | |
|---|---|---|
| 4,939,285 | 7/1990 | Weis et al. |
| 4,950,819 | 8/1990 | Weis et al. |

FOREIGN PATENT DOCUMENTS

| | | |
|---|---|---|
| 0 029 172 | 5/1981 | European Pat. Off. |
| 0299922 | 1/1989 | European Pat. Off. |
| 0310559 | 4/1989 | European Pat. Off. |
| 0321002 | 6/1989 | European Pat. Off. |
| 0 327 496 | 8/1989 | European Pat. Off. |
| 0367714 | 5/1990 | European Pat. Off. |
| 0430876 | 6/1991 | European Pat. Off. |
| 0245207 | 2/1992 | European Pat. Off. |
| 0550211 | 7/1993 | European Pat. Off. |
| 0356633 | 3/1994 | European Pat. Off. |
| 2 256 835 | 6/1974 | Germany. |
| 1 457 535 | 12/1976 | United Kingdom. |

OTHER PUBLICATIONS

Christol, H., et al. *J. Organometal. Chem.* 12:459–470 (1968).

*Primary Examiner*—Michael G. Ambrose
*Attorney, Agent, or Firm*—Connolly and Hutz

[57] ABSTRACT

The invention relates to a process for the preparation of alkali metal salts of phosphonic acid monomethyl esters of the formula (I)

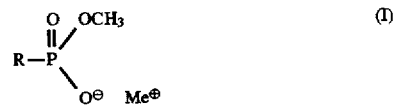

in which

R is $(C_1-C_{14})$-alkyl and

Me is sodium or potassium, which comprises metering 20 to 50% strength alkali metal hydroxide solution, in a molar ratio of 1:1, into phosphonic acid dimethyl esters of the formula (II)

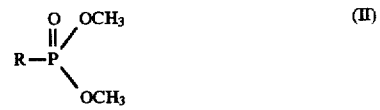

optionally dissolved in water, the total amount of water from the alkali metal hydroxide solution and phosphonic acid dimethyl ester solution being not more than 100% by weight, based on the weight of alkali metal hydroxide and phosphonic acid dimethyl ester, at 90° to 130° C. and distilling off the methanol formed.

9 Claims, No Drawings

PROCESS FOR THE PREPARATION OF ALKALI METAL SALTS OF PHOSPHONIC ACID MONOMETHYL ESTERS

The invention relates to a process for the preparation of alkali metal salts of phosphonic acid monomethyl esters.

Alkali metal salts of phosphonic acid monomethyl esters are valuable agents for flame retardation (cf., for example, EP-PS 0 245 207). Furthermore, the phosphonic acid monomethyl esters, which are very valuable as starting substances for different types of salts of the corresponding phosphonic acid monomethyl esters, for example for the preparation of melamine salts (EP Laid-Open Specification 367 714) or lithium salts or aluminum salts (EP Laid-Open Specification 321 002; EP Laid-Open Specification 356 633; EP Laid-Open Specification 430 876; EP Laid-Open Specification 550 211), can easily be obtained from them. The alkali metal salts of phosphonic acid monomethyl esters can be prepared by reaction of phosphonic acid dimethyl esters with finely ground alkali metal halides, in which methyl chloride is necessarily obtained as a secondary product, which presents great problems because of its carcinogenic potential and is not easy to handle as a gas (EP Laid-Open Specification 310 559). These salts can furthermore be prepared by reaction of phosphonic acid dimethyl esters with alkali metals (EP Laid-Open Specification 299 922). Handling of alkali metals such as lithium or sodium on an industrial scale requires expensive safety measures.

Partial hydrolysis with alkali metal hydroxide solution in water seems to be most simple. Thus, the sodium salt of methanephosphonic acid monomethyl ester is prepared by partial alkaline hydrolysis of methanephosphonic acid dimethyl ester with sodium hydroxide solution in water or in a dioxane/water mixture (H. Cristol et al., J. Organometallic Chem. 12, 459 (1968)). If a 4% strength sodium hydroxide solution is used in this hydrolysis, significant excesses of sodium hydroxide solution are employed, i.e. 0.08 mol of sodium hydroxide solution in a water/dioxane 50:50 mixture per 0.03 mol of phosphonate. This process is not without problems from an industrial aspect, and in particular the high dilution of the alkali, the excess of alkali and the use of an additional water-soluble solvent are disadvantages. The preparation of lithium salts of phosphonic acid methyl esters is described in EP 321 002. Here also, large amounts of water are employed. It is expressly pointed out that this method is unsuitable for the preparation of sodium salts. There was therefore a need to develop a process which avoids the abovementioned disadvantages, can be realized industrially without great expenditure and furthermore renders the desired products accessible both in a high yield and also in a high purity.

Surprisingly, this object is achieved by a process for the preparation of alkali metal salts of phosphonic acid monomethyl esters of the formula I

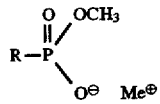

in which
R is $(C_1-C_{14})$-alkyl and
Me is sodium or potassium,
which comprises metering 20 to 50% strength alkali metal hydroxide solution, in a molar ratio of 1:1, into phosphonic acid dimethyl esters of the formula (II)

if appropriate dissolved in water, the total amount of water from the alkali metal hydroxide solution and phosphonic acid dimethyl ester solution being not more than 100% by weight, based on the weight of alkali metal hydroxide and phosphonic acid dimethyl ester, at 90° to 130° C. and distilling off the methanol formed.

The process is important for reaction of compounds of the formula (I) in which R is $(C_1-C_6)$-alkyl, in particular $(C_1-C_3)$-alkyl.

The reaction of methanephosphonic acid dimethyl ester, propanephosphonic acid dimethyl ester, isopropylphosphonic acid dimethyl ester, octanephosphonic acid dimethyl ester and tetradecanephosphonic acid dimethyl ester is of particular interest. Mixtures of phosphonic acid dimethyl esters can also be employed.

The process can be carried out particularly advantageously if the total water content from the alkali metal hydroxide solution and phosphonic acid dimethyl ester solution is between 20 and 80% by weight, in particular between 30 and 70% by weight, preferably between 40 and 60% by weight, based on the weight of alkali metal hydroxide and phosphonic acid dimethyl ester. In many cases, it has proved appropriate to meter in the alkali metal hydroxide solution at a temperature of 100° to 115° C.

The rate of metering in is expediently regulated such that a pH of 10 is not exceeded. Toward the end of the reaction, it is expedient to carry out the metering more slowly.

The methanol formed distills in the course of the reaction.

When the reaction has ended, the concentrated solutions formed from the alkali metal salts of the phosphonic acid monomethyl esters are freed from a residual amount of methanol and from water, if appropriate. The desired end products are then obtained in a practically quantitative yield of high purity.

It is then possible to prepare the corresponding phosphonic acid monomethyl esters by known methods, if desired.

EXAMPLE 1

500 g (4.0 mol) of methanephosphonic acid dimethyl ester and 80 g of water are heated to 100° C. and 320 g (4.0 mol) of 50% strength sodium hydroxide solution are added dropwise, while stirring vigorously. During this procedure, the temperature is increased slowly to 115° C. The dropwise addition is carried out in total for 2 hours, 90% of the total amount being added in about 1 hour and the remaining amount likewise in one hour. The reaction mixture is subsequently stirred for 30 minutes. During the reaction, a total of 139 g of a methanol/water mixture distill off. The residue is evaporated in vacuo. After drying in a vacuum drying cabinet at 80° C., 528 g of methanephosphonic acid monomethyl ester sodium salt are obtained with a purity of 98%, according to 31-P-NMR. The yield is 100% of theory.

EXAMPLE 2

1750 g (14.1 mol) of methanephosphonic acid dimethyl ester and 280 g of water are heated to 106° C. and a solution of 929 g (14.1 mol) of 85% strength potassium hydroxide in 560 g of water is added dropwise in the course of 10 hours, while stirring vigorously. During this procedure, the temperature is increased slowly to 113° C. During the reaction, a total of 433 g of a methanol/water mixture distill off. The residue is evaporated in vacuo. After drying in a vacuum drying cabinet at 80° C., 2080 g of methanephosphonic acid monomethyl ester potassium salt are obtained with a purity of 99%, according to 31-P-NMR. The yield is 100% of theory.

EXAMPLE 3

485 g (3.19 mol) of propanephosphonic acid dimethyl ester and 485 g (2.19 mol) of octanephosphonic acid dimethyl ester are mixed and the mixture is heated to 90° C. 1075 g (5.38 mol) of 20% strength sodium hydroxide solution are now added dropwise in the course of about 23 hours, while stirring vigorously, and at the same time the temperature rises to 100° C. A methanol/water mixture distills off over a Vigreux column. The solution which remains is evaporated in vacuo. A mixture of the propanephosphonic acid monomethyl ester sodium salt and the octanephosphonic acid monomethyl ester sodium salt each having a purity of about 95% is obtained. 962 g of the salts in total are obtained, which corresponds to a yield of 95% of theory.

EXAMPLE 4

973 g (6.4 mol) of propanephosphonic acid dimethyl ester are heated to 90° C. and 1280 g (6.4 mol) of 20% strength sodium hydroxide solution are added dropwise, while stirring vigorously. During this procedure, the temperature is increased slowly to 110° C., and at the same time 238 g of a methanol/water mixture distill off over a Vigreux column. The resulting solution is evaporated in vacuo and the residue which remains is dried in a vacuum drying cabinet. 1020 g of propanephosphonic acid monomethyl ester sodium salt are obtained with a purity of 92%, according to 31-P-NMR. This corresponds to a yield of about 100%.

I claim:

1. A process for the preparation of an alkali metal salt of a phosphonic acid monomethyl ester of the formula I

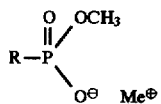 (I)

in which

R is $C_1$–$C_{14}$-alkyl, and

Me is sodium or potassium, which comprises:

providing an aqueous reaction medium by metering of 20 to 50% strength aqueous alkali metal hydroxide solution, in a molar ratio of 1:1, into a phosphonic acid dimethyl ester starting material of the formula II

 (II)

said metering being regulated such that the pH of the aqueous reaction medium does not exceed 10, said phosphonic acid dimethyl ester starting material being optionally dissolved in water, the total water content of said aqueous reaction medium being not more than 100% by weight, based on the weight of alkali metal hydroxide and phosphonic acid dimethyl ester starting material, said reaction medium being maintained at a temperature in the range of 90° to 130° C.; and distilling off methanol produced by the resulting reaction between the aqueous alkali metal hydroxide solution and the phosphonic acid dimethyl ester starting material.

2. The process as claimed in claim 1, wherein R is ($C_1$–$C_6$)-alkyl.

3. The process as claimed in claim 1, wherein formula (II) is methanephosphonic acid dimethyl ester, propanephosphonic acid dimethyl ester, isopropylphosphonic acid dimethyl ester, octanephosphonic acid dimethyl ester or tetradecanephosphonic acid dimethyl ester.

4. The process as claimed in claim 1, wherein the total water content from the alkali metal hydroxide solution and any phosphonic acid dimethyl ester solution is between 20 and 80% by weight, based on the weight of alkali metal hydroxide and phosphonic acid dimethyl ester.

5. The process as claimed in claim 1, wherein the alkali metal hydroxide solution is metered in at 100° to 115° C.

6. The process as claimed in claim 1, wherein R is ($C_1$–$C_3$)-alkyl.

7. The process as claimed in claim 1, wherein the total water content from the alkali metal hydroxide solution and any phosphonic acid dimethyl ester solution is between 30 and 70% by weight, based on the weight of alkali metal hydroxide and phosphonic acid dimethyl ester.

8. The process as claimed in claim 1, wherein the total water content from the alkali metal hydroxide solution and any phosphonic acid dimethyl ester solution is between 40 and 60% by weight, based on the weight of alkali metal hydroxide and phosphonic acid dimethyl ester.

9. The process as claimed in claim 1, wherein a phosphonic acid dimethyl ester of said formula II is dissolved in water, and the total water content includes water from the resulting phosphonic acid dimethyl ester solution.

* * * * *